US008753668B2

(12) United States Patent
Sedmak

(10) Patent No.: US 8,753,668 B2
(45) Date of Patent: Jun. 17, 2014

(54) PRODUCTION OF BETA-GLUCANS AND MANNANS

(75) Inventor: Joseph James Sedmak, Brownsburg, IN (US)

(73) Assignee: Sensient Flavors LLC, Indianapolis, IN (US)

( * ) Notice: Subject to any disclaimer, the term of this patent is extended or adjusted under 35 U.S.C. 154(b) by 967 days.

(21) Appl. No.: 12/693,164

(22) Filed: Jan. 25, 2010

(65) Prior Publication Data

US 2010/0190872 A1 Jul. 29, 2010

Related U.S. Application Data

(63) Continuation of application No. 11/418,922, filed on May 5, 2006, now abandoned.

(60) Provisional application No. 60/677,973, filed on May 5, 2005.

(51) Int. Cl.
*A23K 1/06* (2006.01)

(52) U.S. Cl.
USPC ............ 424/442; 514/777; 426/635; 426/615

(58) Field of Classification Search
None
See application file for complete search history.

(56) References Cited

U.S. PATENT DOCUMENTS

| | | | |
|---|---|---|---|
| 3,495,990 A | 2/1970 | Kayser |
| 3,754,925 A | 8/1973 | Kimura et al. |
| 3,822,250 A | 7/1974 | Kimura et al. |
| 3,867,554 A | 2/1975 | Sucher et al. |
| 3,880,742 A | 4/1975 | James et al. |
| 3,934,039 A | 1/1976 | Cardini et al. |
| 3,943,247 A | 3/1976 | Komatsu et al. |
| 3,961,080 A | 6/1976 | Sugimoto et al. |
| 3,973,008 A | 8/1976 | Sugiyama et al. |
| 3,975,553 A | 8/1976 | Griffon |
| 3,989,847 A | 11/1976 | Kurihara et al. |
| 4,016,295 A | 4/1977 | Burrows et al. |
| 4,036,993 A | 7/1977 | Ikeda et al. |
| 4,041,152 A | 8/1977 | Chany et al. |
| 4,041,181 A | 8/1977 | Burrows et al. |
| 4,066,793 A | 1/1978 | Eguchi |
| 4,072,567 A | 2/1978 | Yokobayashi et al. |
| 4,075,405 A | 2/1978 | Takahashi et al. |
| 4,088,539 A | 5/1978 | Muller |
| 4,122,196 A | 10/1978 | Robbins et al. |
| 4,138,479 A | 2/1979 | Truscheit et al. |
| 4,158,607 A | 6/1979 | Kalinowski et al. |
| 4,207,344 A | 6/1980 | Cerrillo |
| 4,211,645 A | 7/1980 | Zajic et al. |
| 4,216,293 A | 8/1980 | Fedeli et al. |
| 4,218,481 A | 8/1980 | Chao et al. |
| 4,244,973 A | 1/1981 | Van Megen |
| 4,247,541 A | 1/1981 | Ishida et al. |
| 4,247,574 A | 1/1981 | Utena et al. |
| 4,279,653 A | 7/1981 | Makishima et al. |
| 4,285,976 A | 8/1981 | Akin et al. |
| 4,295,889 A | 10/1981 | Eida et al. |
| 4,299,630 A | 11/1981 | Hwang |
| 4,303,680 A | 12/1981 | Tanekawa et al. |
| 4,310,553 A | 1/1982 | Odintsova |
| 4,311,714 A | 1/1982 | Goering et al. |
| 4,311,717 A | 1/1982 | McGinley |
| 4,313,934 A | 2/1982 | Kitamura et al. |
| 4,332,894 A | 6/1982 | Whistler |
| 4,339,360 A | 7/1982 | Shimizu et al. |
| 4,340,675 A | 7/1982 | Johansen |
| 4,344,968 A | 8/1982 | Aoda et al. |
| 4,361,843 A | 11/1982 | Cooke et al. |
| 4,368,322 A | 1/1983 | Muzzarelli |
| 4,381,946 A | 5/1983 | Yehara et al. |
| 4,383,859 A | 5/1983 | Moore et al. |
| 4,388,115 A | 6/1983 | Sugiyama et al. |
| 4,427,710 A | 1/1984 | Terada et al. |
| 4,454,315 A | 6/1984 | Sasaki et al. |
| 4,477,655 A | 10/1984 | Holmes |
| 4,484,012 A | 11/1984 | Stahl et al. |
| 4,500,355 A | 2/1985 | Shimada et al. |
| 4,508,570 A | 4/1985 | Fujii et al. |
| 4,508,745 A | 4/1985 | Fulger et al. |
| 4,513,019 A | 4/1985 | Brancq et al. |

(Continued)

FOREIGN PATENT DOCUMENTS

| | | |
|---|---|---|
| AU | 75860/91 | 4/1995 |
| AU | 2003258181 | 2/2004 |
| BE | 662884 | 10/1965 |
| CA | 1074453 | 3/1980 |
| CA | 2072145 | 5/1991 |
| CA | 2208896 | 12/1997 |
| CA | 2501889 | 2/2005 |
| DE | 3741583 | 6/1988 |
| DE | 19835767 | 2/2000 |
| EP | 0133827 | 7/1984 |

(Continued)

OTHER PUBLICATIONS

U.S. Appl. No. 11/418,922 dated Jul. 23, 2009 (8 pages).
U.S. Appl. No. 11/418,922 dated Nov. 21, 2008 (6 pages).
International Search Report for Application No. PCT/US2006/017270 dated Sep. 25, 2006 (5 pages).
International Preliminary Report on Patentability and Written Opinion for Application No. PCT/US2006/017270 dated Nov. 15, 2007 (9 pages).
Chinese Patent Office Action for Application No. 200680015026.7 dated Dec. 18, 2009 (11 pages).

(Continued)

*Primary Examiner* — Jon P Weber
*Assistant Examiner* — Tiffany Gough
(74) *Attorney, Agent, or Firm* — Michael Best & Friedrich LLP

(57) ABSTRACT

Disclosed are methods for producing yeast β-glucan and mannan preparations. The methods employ an autolysis process, followed by enzymatic treatment with one or more of a protease, glucanase or lipase. The preparations produced may be used in food supplements, pharmaceuticals, cosmetics, animal feeds, and neutraceuticals.

7 Claims, 2 Drawing Sheets

(56) References Cited

U.S. PATENT DOCUMENTS

| | | |
|---|---|---|
| 4,526,794 A | 7/1985 | Altomare et al. |
| 4,543,370 A | 9/1985 | Porter et al. |
| 4,544,552 A | 10/1985 | Fraefel et al. |
| 4,572,832 A | 2/1986 | Kigasawa et al. |
| 4,576,646 A | 3/1986 | Branco et al. |
| 4,584,197 A | 4/1986 | Takasaki et al. |
| 4,587,285 A | 5/1986 | Ayla et al. |
| 4,588,827 A | 5/1986 | Mueller et al. |
| 4,620,876 A | 11/1986 | Fujii et al. |
| 4,623,624 A | 11/1986 | Schultze |
| 4,652,455 A | 3/1987 | Sugino et al. |
| 4,659,388 A | 4/1987 | Innami et al. |
| 4,676,976 A | 6/1987 | Toba et al. |
| 4,692,094 A | 9/1987 | Kulinyak |
| 4,692,404 A | 9/1987 | Ashihara et al. |
| 4,707,471 A | 11/1987 | Larm et al. |
| 4,731,248 A | 3/1988 | Hogan et al. |
| 4,737,190 A | 4/1988 | Shimada et al. |
| 4,739,046 A | 4/1988 | Di Luzio |
| 4,741,907 A | 5/1988 | Furuhashi |
| 4,749,566 A | 6/1988 | Casellas et al. |
| 4,759,942 A | 7/1988 | Von Fulger |
| 4,761,402 A | 8/1988 | Williams et al. |
| 4,761,405 A | 8/1988 | Rzeszotarski et al. |
| 4,765,992 A | 8/1988 | Geneix et al. |
| 4,769,363 A | 9/1988 | Misaki et al. |
| 4,774,093 A | 9/1988 | Provonchee et al. |
| 4,793,860 A | 12/1988 | Murakami et al. |
| 4,795,653 A | 1/1989 | Bommarito |
| 4,795,745 A | 1/1989 | Larm et al. |
| 4,798,730 A | 1/1989 | Scoville et al. |
| 4,804,545 A | 2/1989 | Goering et al. |
| 4,806,474 A | 2/1989 | Hershberger |
| 4,808,419 A | 2/1989 | Hsu |
| 4,810,509 A | 3/1989 | Kanegae et al. |
| 4,810,646 A | 3/1989 | Jamas et al. |
| 4,818,751 A | 4/1989 | Ibe |
| 4,818,752 A | 4/1989 | Williams et al. |
| 4,833,131 A | 5/1989 | Williams et al. |
| 4,835,265 A | 5/1989 | Muzzarelli |
| 4,859,488 A | 8/1989 | Kam et al. |
| 4,863,746 A | 9/1989 | Uchida et al. |
| 4,871,571 A | 10/1989 | Jensen et al. |
| 4,876,103 A | 10/1989 | Kawano et al. |
| 4,877,777 A | 10/1989 | DiLuzio |
| 4,882,160 A | 11/1989 | Yang et al. |
| 4,891,220 A | 1/1990 | Donzis |
| 4,900,571 A | 2/1990 | Kammuri et al. |
| 4,900,722 A | 2/1990 | Williams et al. |
| 4,942,540 A | 7/1990 | Black et al. |
| 4,943,444 A | 7/1990 | Nozaki et al. |
| 4,948,598 A | 8/1990 | Lembke et al. |
| 4,950,749 A | 8/1990 | Johal et al. |
| 4,962,094 A | 10/1990 | Jamas et al. |
| 4,965,347 A | 10/1990 | Misaki et al. |
| 4,975,421 A | 12/1990 | Williams et al. |
| 4,978,551 A | 12/1990 | Sugino |
| 4,981,700 A | 1/1991 | Sarishvili et al. |
| 4,986,999 A | 1/1991 | Takasaki et al. |
| 4,992,540 A | 2/1991 | Jamas et al. |
| 4,994,285 A | 2/1991 | Hisano et al. |
| 5,008,125 A | 4/1991 | Cale et al. |
| 5,017,224 A | 5/1991 | Tomita et al. |
| 5,028,703 A | 7/1991 | Jamas et al. |
| 5,032,401 A | 7/1991 | Jamas et al. |
| 5,037,972 A | 8/1991 | Jamas et al. |
| 5,057,503 A | 10/1991 | Czop et al. |
| 5,082,936 A | 1/1992 | Jamas et al. |
| 5,084,386 A | 1/1992 | Tuse et al. |
| 5,089,285 A | 2/1992 | Nozaki et al. |
| 5,116,631 A | 5/1992 | Sakamoto et al. |
| 5,118,673 A | 6/1992 | Carpenter et al. |
| 5,147,862 A | 9/1992 | Nikl et al. |
| 5,158,772 A | 10/1992 | Davis |
| 5,165,968 A | 11/1992 | Johnson et al. |
| 5,167,708 A | 12/1992 | Wilhelm et al. |
| 5,185,327 A | 2/1993 | Matsuzaki et al. |
| 5,188,852 A | 2/1993 | Ongane et al. |
| 5,189,028 A | 2/1993 | Nikl et al. |
| 5,191,016 A | 3/1993 | Yalpani |
| 5,194,600 A | 3/1993 | Bussey et al. |
| 5,223,491 A | 6/1993 | Donzis |
| 5,250,436 A | 10/1993 | Jamas et al. |
| 5,273,772 A | 12/1993 | Cooper |
| 5,288,704 A | 2/1994 | Ungheri et al. |
| 5,308,838 A | 5/1994 | McAnalley et al. |
| 5,314,872 A | 5/1994 | Kato et al. |
| 5,322,841 A | 6/1994 | Jamas et al. |
| 5,332,667 A | 7/1994 | Kado et al. |
| 5,342,626 A | 8/1994 | Winston, Jr. et al. |
| 5,358,731 A | 10/1994 | Jakamoto |
| 5,364,462 A | 11/1994 | Crystal et al. |
| 5,369,029 A | 11/1994 | Broker et al. |
| 5,378,232 A | 1/1995 | Easton et al. |
| 5,387,423 A | 2/1995 | Emoto et al. |
| 5,387,427 A | 2/1995 | Lawrence et al. |
| 5,393,333 A | 2/1995 | Trouve |
| 5,397,773 A | 3/1995 | Donzis |
| 5,401,727 A | 3/1995 | Rorstad et al. |
| 5,422,133 A | 6/1995 | Yamamoto et al. |
| 5,428,383 A | 6/1995 | Shields et al. |
| 5,429,828 A | 7/1995 | Fodge et al. |
| 5,441,943 A | 8/1995 | McAnalley et al. |
| 5,447,505 A | 9/1995 | Valentine et al. |
| 5,449,526 A | 9/1995 | Kawano |
| 5,458,893 A | 10/1995 | Smith |
| 5,462,755 A | 10/1995 | Mehnert |
| 5,468,510 A | 11/1995 | Christensen et al. |
| 5,468,737 A | 11/1995 | McAnalley et al. |
| 5,480,662 A | 1/1996 | Boode-Boissevain et al. |
| 5,488,040 A | 1/1996 | Jamas et al. |
| 5,488,402 A | 1/1996 | Shields et al. |
| 5,496,544 A | 3/1996 | Mellul et al. |
| 5,504,079 A | 4/1996 | Jamas et al. |
| 5,506,124 A | 4/1996 | Jamas et al. |
| 5,506,210 A | 4/1996 | Parish et al. |
| 5,512,287 A | 4/1996 | Wang et al. |
| 5,518,710 A | 5/1996 | Bhatty |
| 5,519,009 A | 5/1996 | Donzis |
| 5,519,287 A | 5/1996 | Goodale et al. |
| 5,523,088 A | 6/1996 | Ritchie et al. |
| 5,532,223 A | 7/1996 | Jamas et al. |
| 5,543,302 A | 8/1996 | Boguslawski et al. |
| 5,545,557 A | 8/1996 | Hobson et al. |
| 5,554,386 A | 9/1996 | Groman et al. |
| 5,565,234 A | 10/1996 | Teraguchi et al. |
| 5,570,015 A | 10/1996 | Takaishi et al. |
| 5,574,023 A | 11/1996 | Shibata et al. |
| 5,576,015 A | 11/1996 | Donzis |
| 5,587,364 A | 12/1996 | McAnalley et al. |
| 5,589,591 A | 12/1996 | Lewis |
| 5,595,571 A | 1/1997 | Jaffe et al. |
| 5,599,697 A | 2/1997 | Kanegae et al. |
| 5,607,677 A | 3/1997 | Jamas et al. |
| 5,614,242 A | 3/1997 | Fox |
| 5,622,939 A | 4/1997 | Jamas et al. |
| 5,622,940 A | 4/1997 | Ostroff |
| 5,626,874 A | 5/1997 | Conte et al. |
| 5,654,028 A | 8/1997 | Christensen et al. |
| 5,663,324 A | 9/1997 | James et al. |
| 5,681,583 A | 10/1997 | Conte et al. |
| 5,686,296 A | 11/1997 | Hobson et al. |
| 5,688,931 A | 11/1997 | Nogusa et al. |
| 5,690,981 A | 11/1997 | Watanabe et al. |
| 5,695,970 A | 12/1997 | Yu et al. |
| 5,702,719 A | 12/1997 | Donzis |
| 5,703,060 A | 12/1997 | McAnalley et al. |
| 5,705,184 A | 1/1998 | Donzis |
| 5,712,110 A | 1/1998 | Flen et al. |
| 5,716,652 A | 2/1998 | Greenberg et al. |
| 5,718,932 A | 2/1998 | Nakao et al. |
| 5,720,777 A | 2/1998 | Jaffe et al. |
| 5,725,901 A | 3/1998 | Fox |
| 5,741,495 A | 4/1998 | Jamas et al. |

(56) References Cited

U.S. PATENT DOCUMENTS

| | | |
|---|---|---|
| 5,747,045 A | 5/1998 | Ritchie et al. |
| 5,753,266 A | 5/1998 | Youssefyeh et al. |
| 5,760,702 A | 6/1998 | Ito et al. |
| 5,773,227 A | 6/1998 | Kuhn et al. |
| 5,773,425 A | 6/1998 | McAnalley et al. |
| 5,773,427 A | 6/1998 | Day |
| 5,780,453 A | 7/1998 | McAnalley et al. |
| 5,783,569 A | 7/1998 | Jamas et al. |
| 5,785,975 A | 7/1998 | Parikh |
| 5,786,342 A | 7/1998 | Carpenter et al. |
| 5,795,979 A | 8/1998 | Kusatsu et al. |
| 5,807,559 A | 9/1998 | Jondal |
| 5,811,542 A | 9/1998 | Jamas et al. |
| 5,817,643 A | 10/1998 | Jamas et al. |
| 5,827,529 A | 10/1998 | Ono et al. |
| 5,827,937 A | 10/1998 | Agerup |
| 5,843,180 A | 12/1998 | Jaffe et al. |
| 5,843,181 A | 12/1998 | Jaffe et al. |
| 5,849,720 A | 12/1998 | Jamas et al. |
| 5,861,048 A | 1/1999 | Kamasaka et al. |
| 5,871,966 A | 2/1999 | Kofod et al. |
| 5,885,617 A | 3/1999 | Jordan |
| 5,888,984 A | 3/1999 | Brown |
| 5,902,607 A | 5/1999 | Taylor |
| 5,902,796 A | 5/1999 | Shand et al. |
| 5,912,153 A | 6/1999 | Selitrennikoff et al. |
| 5,922,118 A | 7/1999 | Johnson et al. |
| 5,932,561 A | 8/1999 | Meyers et al. |
| 5,939,129 A | 8/1999 | Kawano |
| 5,955,072 A | 9/1999 | Takahasi et al. |
| 5,958,755 A | 9/1999 | Skelton et al. |
| 5,968,811 A | 10/1999 | Greenshields |
| 5,972,642 A | 10/1999 | Flen et al. |
| 5,976,580 A | 11/1999 | Ivey et al. |
| 5,985,891 A | 11/1999 | Rowe |
| 5,989,552 A | 11/1999 | McKenzie et al. |
| 6,020,016 A | 2/2000 | Castleberry |
| 6,020,324 A | 2/2000 | Jamas et al. |
| 6,020,422 A | 2/2000 | Connors et al. |
| 6,036,946 A | 3/2000 | Greene |
| 6,046,323 A | 4/2000 | Park |
| 6,056,981 A | 5/2000 | Saxby |
| 6,060,429 A | 5/2000 | Ben-Shalom et al. |
| 6,080,222 A | 6/2000 | Kawamoto |
| 6,080,442 A | 6/2000 | Yoshikawa et al. |
| 6,083,547 A | 7/2000 | Katta et al. |
| 6,084,092 A | 7/2000 | Wakshull et al. |
| 6,090,938 A | 7/2000 | Wakshull et al. |
| 6,093,426 A | 7/2000 | Tai et al. |
| 6,093,552 A | 7/2000 | Laine et al. |
| 6,099,876 A | 8/2000 | Nussinovitch |
| 6,110,692 A | 8/2000 | Wakshull et al. |
| 6,117,850 A | 9/2000 | Patchen et al. |
| 6,132,750 A | 10/2000 | Perrier et al. |
| 6,143,551 A | 11/2000 | Goebel |
| 6,143,731 A | 11/2000 | Jamas et al. |
| 6,143,883 A | 11/2000 | Lehmann et al. |
| 6,146,684 A | 11/2000 | Kawano |
| 6,149,940 A | 11/2000 | Maggi et al. |
| 6,159,504 A | 12/2000 | Kumabe |
| 6,165,994 A | 12/2000 | Henley |
| 6,168,799 B1 | 1/2001 | Klein |
| 6,177,256 B1 | 1/2001 | McKenzie et al. |
| 6,180,159 B1 | 1/2001 | Villagran et al. |
| 6,194,191 B1 | 2/2001 | Zhang et al. |
| 6,197,952 B1 | 3/2001 | Fox |
| 6,210,677 B1 | 4/2001 | Bohannon |
| 6,210,686 B1 | 4/2001 | Bell et al. |
| 6,214,337 B1 | 4/2001 | Hayen et al. |
| 6,214,376 B1 | 4/2001 | Gennadios |
| 6,228,391 B1 | 5/2001 | Shimizu et al. |
| 6,235,272 B1 | 5/2001 | Greene |
| 6,242,594 B1 | 6/2001 | Kelly |
| 6,248,566 B1 | 6/2001 | Imanaka et al. |
| 6,251,877 B1 | 6/2001 | Park et al. |
| 6,254,869 B1 | 7/2001 | Petersen et al. |
| 6,255,291 B1 | 7/2001 | Germano |
| 6,268,182 B1 | 7/2001 | Kamasaka et al. |
| 6,271,215 B1 | 8/2001 | Parish et al. |
| 6,274,370 B1 | 8/2001 | Hobson et al. |
| 6,280,740 B1 | 8/2001 | Gupta et al. |
| 6,284,509 B1 | 9/2001 | Ferrer et al. |
| 6,284,885 B1 | 9/2001 | Tamura et al. |
| 6,284,886 B1 | 9/2001 | Redmond |
| 6,287,612 B1 | 9/2001 | Mandova et al. |
| 6,291,671 B1 | 9/2001 | Ihoue et al. |
| 6,306,453 B1 | 10/2001 | Kurzinger |
| 6,307,038 B1 | 10/2001 | Takahashi et al. |
| 6,323,338 B1 | 11/2001 | Potter et al. |
| 6,342,486 B1 | 1/2002 | Zulli et al. |
| 6,352,698 B1 | 3/2002 | Castelli et al. |
| 6,355,625 B1 | 3/2002 | Pavliak et al. |
| 6,365,176 B1 | 4/2002 | Bell et al. |
| 6,365,185 B1 | 4/2002 | Ritschel et al. |
| 6,369,216 B1 | 4/2002 | Patchen et al. |
| 6,379,725 B1 | 4/2002 | Wang et al. |
| 6,395,314 B1 | 5/2002 | Whalen et al. |
| 6,423,832 B1 | 7/2002 | Seljelid |
| 6,426,077 B1 | 7/2002 | Grace et al. |
| 6,426,201 B1 | 7/2002 | Morgan |
| 6,444,448 B1 | 9/2002 | Wheatcroft et al. |
| 6,448,323 B1 | 9/2002 | Jordan et al. |
| 6,455,083 B1 | 9/2002 | Wang |
| 6,455,090 B1 | 9/2002 | Uzuhashi et al. |
| 6,465,218 B1 | 10/2002 | Horiuchi et al. |
| 6,476,003 B1 | 11/2002 | Jordan et al. |
| 6,482,632 B1 | 11/2002 | Agrawal et al. |
| 6,482,802 B1 | 11/2002 | Hu et al. |
| 6,482,942 B1 | 11/2002 | Vittori |
| 6,485,945 B1 | 11/2002 | Potter et al. |
| 6,486,314 B1 | 11/2002 | Van Geel-Schutten et al. |
| 6,488,929 B2 | 12/2002 | Cutter et al. |
| 6,488,955 B1 | 12/2002 | Decombaz et al. |
| 6,517,829 B1 | 2/2003 | Frenken et al. |
| RE38,047 E | 3/2003 | Fodge et al. |
| 6,531,178 B2 | 3/2003 | Cahill, Jr. et al. |
| 6,534,083 B2 | 3/2003 | Gilding et al. |
| 6,541,678 B2 | 4/2003 | Klein |
| 6,548,075 B1 | 4/2003 | Bengs et al. |
| 6,548,643 B1 | 4/2003 | McKenzie et al. |
| 6,562,459 B1 | 5/2003 | Bengs et al. |
| 6,566,516 B1 | 5/2003 | Sunamoto et al. |
| 6,569,475 B2 | 5/2003 | Song et al. |
| 6,573,245 B1 | 6/2003 | Marciani |
| 6,576,015 B2 | 6/2003 | Geistlich et al. |
| 6,576,307 B2 | 6/2003 | Otsu et al. |
| 6,592,897 B1 | 7/2003 | Bengs et al. |
| 6,592,914 B1 | 7/2003 | Triantafyllou |
| 6,593,470 B1 | 7/2003 | Bengs et al. |
| 6,607,775 B2 | 8/2003 | Aldred et al. |
| 6,624,300 B2 | 9/2003 | Potter et al. |
| 6,630,310 B2 | 10/2003 | Wakshull et al. |
| 6,635,275 B1 | 10/2003 | Scott et al. |
| 6,635,633 B2 | 10/2003 | Cai et al. |
| 6,656,481 B1 | 12/2003 | Shiku et al. |
| 6,669,771 B2 | 12/2003 | Tokiwa et al. |
| 6,669,975 B2 | 12/2003 | Abene et al. |
| 6,673,384 B1 | 1/2004 | Villagran et al. |
| 6,677,142 B1 | 1/2004 | Weissmueller et al. |
| 6,680,184 B2 | 1/2004 | Nussinovitch |
| 6,699,694 B1 | 3/2004 | Buttcher et al. |
| 6,703,062 B1 | 3/2004 | Appleqvist |
| 6,706,305 B2 | 3/2004 | Wolt et al. |
| 6,713,450 B2 | 3/2004 | Frangione et al. |
| 6,713,459 B1 | 3/2004 | Williams et al. |
| 6,716,462 B2 | 4/2004 | Prosise et al. |
| 6,720,015 B2 | 4/2004 | Prosise et al. |
| 6,726,943 B2 | 4/2004 | Prosise et al. |
| 6,737,089 B2 | 5/2004 | Wadsworth et al. |
| 6,749,885 B2 | 6/2004 | Cahill, Jr. et al. |
| 6,797,307 B2 | 9/2004 | Malkki et al. |
| 6,811,788 B2 | 11/2004 | Yu |
| 6,824,810 B2 | 11/2004 | Sargent et al. |
| 6,827,954 B2 | 12/2004 | Prosise et al. |

(56) References Cited

U.S. PATENT DOCUMENTS

| | | |
|---|---|---|
| 6,831,173 B1 | 12/2004 | Jetten et al. |
| 6,835,214 B2 | 12/2004 | Kitano et al. |
| 6,835,558 B2 | 12/2004 | Van Lengerich et al. |
| 6,846,501 B2 | 1/2005 | Prosise et al. |
| 6,852,333 B1 | 2/2005 | Cook |
| 6,858,214 B1 | 2/2005 | Kropf et al. |
| 6,858,244 B2 | 2/2005 | Kuroda et al. |
| 6,875,754 B1 | 4/2005 | Griesbach et al. |
| 6,875,861 B1 | 4/2005 | Besemer et al. |
| 6,887,307 B1 | 5/2005 | Scott et al. |
| 6,896,918 B2 | 5/2005 | Yokomizo |
| 6,897,046 B2 | 5/2005 | Horiuchi et al. |
| 6,899,892 B2 | 5/2005 | Gallaher et al. |
| 6,899,905 B2 | 5/2005 | Prosise et al. |
| 6,908,885 B2 | 6/2005 | Bengs et al. |
| 6,911,436 B2 | 6/2005 | Brown et al. |
| 6,919,312 B2 | 7/2005 | Mochizuki et al. |
| 6,929,807 B1 | 8/2005 | McAnalley et al. |
| 6,936,598 B2 | 8/2005 | Khoo et al. |
| 6,939,864 B1 | 9/2005 | Johnson et al. |
| 2002/0032170 A1 | 3/2002 | Jamas et al. |
| 2002/0107226 A1 | 8/2002 | Berlin et al. |
| 2002/0143174 A1 | 10/2002 | Patchen et al. |
| 2002/0146463 A1 | 10/2002 | Clayton |
| 2003/0012819 A1 | 1/2003 | Ko et al. |
| 2003/0059416 A1 | 3/2003 | Slinde et al. |
| 2003/0124597 A1 | 7/2003 | Cheung |
| 2003/0130205 A1 | 7/2003 | Christian |
| 2003/0153746 A1 | 8/2003 | Van Lengerich et al. |
| 2003/0154974 A1 | 8/2003 | Morgan |
| 2003/0165604 A1 | 9/2003 | Tsubaki et al. |
| 2003/0219468 A1 | 11/2003 | Raczek et al. |
| 2004/0014320 A1 | 1/2004 | Chen |
| 2004/0014715 A1 | 1/2004 | Ostroff |
| 2004/0023923 A1 | 2/2004 | Morgan |
| 2004/0054166 A1 | 3/2004 | Sauter et al. |
| 2004/0058889 A1 | 3/2004 | Sorgente et al. |
| 2004/0082539 A1 | 4/2004 | Kelly |
| 2004/0116379 A1 | 6/2004 | Cheung |
| 2004/0116380 A1 | 6/2004 | Jamas et al. |
| 2004/0127458 A1 | 7/2004 | Hunter et al. |
| 2004/0258829 A1 | 12/2004 | Zheng et al. |
| 2005/0008679 A1 | 1/2005 | Bedding et al. |
| 2005/0020490 A1 | 1/2005 | Courie, Jr. et al. |
| 2005/0058671 A1 | 3/2005 | Bedding et al. |
| 2005/0069989 A1 | 3/2005 | Kim et al. |
| 2005/0170062 A1 | 8/2005 | Burling et al. |
| 2008/0193485 A1 | 8/2008 | Gorbach et al. |
| 2008/0194517 A1 | 8/2008 | Smith |

FOREIGN PATENT DOCUMENTS

| | | |
|---|---|---|
| EP | 0153680 | 2/1985 |
| EP | 0273000 | 4/1987 |
| EP | 0416343 | 8/1990 |
| EP | 0440725 | 8/1991 |
| EP | 0515216 | 5/1992 |
| EP | 0566347 | 10/1993 |
| EP | 0664671 | 8/1995 |
| EP | 0507952 | 12/1996 |
| EP | 0500718 | 1/1997 |
| EP | 0466037 | 12/1997 |
| EP | 0811690 | 12/1997 |
| EP | 0553176 | 6/1999 |
| EP | 0954978 | 5/2001 |
| EP | 1283261 | 2/2003 |
| EP | 1480529 | 9/2003 |
| FR | 2470598 | 11/1980 |
| FR | 2660317 | 3/1990 |
| FR | 2836333 | 2/2002 |
| GB | 1003976 | 9/1965 |
| GB | 1025139 | 4/1966 |
| GB | 1502902 | 3/1978 |
| GB | 1531498 | 11/1978 |
| JP | 53044614 | 4/1978 |
| JP | 55000709 | 1/1980 |
| JP | 60196195 | 10/1985 |
| JP | 60238139 | 11/1985 |
| JP | 61167622 | 7/1986 |
| JP | 61291509 | 12/1986 |
| JP | 62040262 | 2/1987 |
| JP | 62201901 | 9/1987 |
| JP | 3176418 | 7/1991 |
| JP | 3204804 | 9/1991 |
| JP | 7184595 | 7/1995 |
| JP | 7308157 | 11/1995 |
| JP | 7313069 | 12/1995 |
| JP | 9084529 | 3/1997 |
| JP | 2001008636 | 1/2001 |
| JP | 2004099580 | 4/2004 |
| WO | WO 90/04334 | 5/1990 |
| WO | WO 91/07091 | 5/1991 |
| WO | WO 92/07064 | 4/1992 |
| WO | WO 94/03500 | 2/1994 |
| WO | WO 94/04163 | 3/1994 |
| WO | WO 94/14953 | 7/1994 |
| WO | WO 95/04467 | 2/1995 |
| WO | WO 96/07329 | 3/1996 |
| WO | WO 96/38057 | 12/1996 |
| WO | WO 97/02356 | 1/1997 |
| WO | WO 97/38129 | 4/1997 |
| WO | WO 97/28700 | 8/1997 |
| WO | WO 97/38293 | 10/1997 |
| WO | WO 98/13056 | 4/1998 |
| WO | WO 98/39014 | 9/1998 |
| WO | WO 99/24020 | 5/1999 |
| WO | WO 99/31269 | 6/1999 |
| WO | WO 99/67419 | 12/1999 |
| WO | WO 00/08201 | 2/2000 |
| WO | WO 00/12590 | 3/2000 |
| WO | WO 02/12348 | 2/2002 |
| WO | WO 02/14317 | 2/2002 |
| WO | WO 02/32170 | 4/2002 |
| WO | WO 03/068824 | 8/2003 |
| WO | WO 03/081882 | 10/2003 |
| WO | WO 2004/014320 | 2/2004 |
| WO | WO 2004/014715 | 2/2004 |
| WO | WO 2004/021994 | 3/2004 |
| WO | WO 2004/026277 | 4/2004 |
| WO | WO 2004/026968 | 4/2004 |
| WO | WO 2004/030613 | 4/2004 |
| WO | WO 2004/078788 | 9/2004 |
| WO | WO 2006/042403 | 4/2006 |

OTHER PUBLICATIONS

European Patent Office Action for Application No. 06759096.8 dated Apr. 23, 2010 (3 pages).

Chinese Patent Office Action for Application No. 200680015026.7 dated Mar. 14, 2011 (5 pages).

European Patent Office Action for Application No. 06759096.8 dated Nov. 18, 2011 (7 pages).

Mexican Patent Office Action for Application No. MX/A/2007/013725 dated Oct. 17, 2011 (3 pages) English translation only.

Japanese Patent Office Action for Application No. 2008-510230 dated Nov. 15, 2011 (4 pages).

Chinese Patent Office Action for Application No. 200680015026.7 dated Feb. 6, 2012 (4 pages).

European Patent Office Action for Application No. 06759096.8 dated May 4, 2012 (6 pages).

Mexican Patent Office Action for Application No. MX/A/2007/013725 dated May 18, 2012 (2 pages) English translation only.

Mexican Patent Office Action for Application No. MX/a/2007/013725 dated May 20, 2011 (4 pages).

Babayan, T.L. et al., "Isolation of physiologically active mannan and other polysaccharides from autolysate of baker's yeast," Biotekhnologiya (1992) 2:23-26.

Bacon, J.S.D. et al., "The glucan components of the cell wall of baker's yeast (*Saccharomyces cerevisiae*) considered in relation to its ultrastructure," Biochem. J. (1969) 114:557-567.

(56) References Cited

OTHER PUBLICATIONS

Ballou, C., "Some aspects of the structure, immunochemistry, and genetic control of yeast mannans," Adv. Enzymol. (1974) 40:239-270.

Ballou, C., "Structure and biosynthesis of the mannan component of the yeast cell envelope," Adv. Microbiol. Physiol. (1976) 14:93-158.

Behall, K.M. et al., "Effect of beta-glucan level in oat fiber extracts on blood lipids in men and women," J. Amer. Coll. Nutri. (1997) 16(1):46-51.

Bell, D.J. et al., "The structure of a cell wall of baker's yeast," J. Chem. Soc. (1950) 1944-1947.

Bonaly, R. et al., "Etude des parois de levures du genre rhodotorula. II. Influence des conditions de culture sur la composition climique des parois," Biochim. Biophys. Acta (1971) 244:484-494.

Braaten, J.T. et al., "Oat beta-glucan reduces blood cholesterol concentration in hypercholesterolemic subjects," Eur. J. Clin. Nutri. (1994) 48(7):465-474.

Cabib, E. et al., "Chitin and yeast budding," J. Biol. Chem. (1971) 246(1):152-159.

Cid, V.J. et al., "Molecular basis of cell integrity and morphogenesis in Saccharomyces cerevisiae," Microbiol. Reviews (1995) 59:345-386.

Conway, J. et al., "The effect of the addition of proteases and glucanases during yeast autolysis on the production and properties of yeast extracts," Can. J. Microbiol. (2001) 47(1):18-24 (Abstract).

Fleet, G.H. et al., "Isolation and composition of an alkali-soluble glucan from the cell walls of Saccharomyces cerevisiae," J. Gen. Microbio. (1976) 94:180-192.

Freimund, S. et al., "A new non-degrading isolation process for 1,3-beta-d-glucan of high purity from baker's yeast Saccharomyces cerevisiae," Carbohydrate Polymers (2003) 54(2):159-171.

Hernawan, T. et al., "Chemical and cytological changes during the autolysis of yeasts," J. Indust. Microb. (1995) 14:440-450.

Jamas et al., "Morphology of yeast cell wall as affected by genetic manipulation of B(1-6) glycosidic linkage," Biotech. Bioengineering (1986) 28:769-784.

Jung, P. et al., "Identification of the lipid intermediate in yeast mannan biosynthesis," Eur. J. Biochem. (1973) 37:1-6.

Kath, F. et al., "Mild enzymatic isolation of mannan and glucan from yeast Saccharomyces cerevisiae," Die Angewandte Makromolekulare Chemie (1999) 268(1):59-68 (Abstract).

Klis, F.M. et al., "Review: Cell wall assembly in yeast," Yeast (1994) 10:851-869.

Kopecka, M., "Electron microscopic study of purified polysaccharide components glucans and mannan of the cell walls in the yeast Saccharomyces cerevisiae," J. Basic Microbio. (1985) 25(3):161-174.

Lehninger, A.L., Biochemistry, 2$^{nd}$ Edition, Worth Publishers, Inc., NY (1978) 220-221.

Lipke, P.N. et al., "Cell wall architecture in yeast: new structure and new challenges," J. Bacter. (1998) 180(15):3735-3740.

Manners et al., "The structure of a β-(1→6)-D-glucan from yeast cell walls," Biochem. J. (1973) 135:31-36.

Manners, D.J. et al., "The structure of a β-(1→3)-D-glucan from yeast cell walls," Biochem. J. (1973) 135:19-30.

Nakajima, T. et al., "Characterization of the carbohydrate fragments obtained from Saccharomyces cerevisiae mannan by alkaline degradation," J. Biol. Chem. (1974) 249(23):7679-7684.

Okubo, Y. et al., "Relationship between phosphate content and immunochemical properties of subfractions of bakers' yeast mannan," J. Bacteriol. (1978) 136(1):63-68.

Pastor, F.I.J. et al., "Structure of the Saccharomyces cerevisiae cell wall. Mannoproteins released by zymolyase and their contribution to wall architecture," Biochimica et Biophysica Acta (1984) 802:292-300.

Peat, S. et al., "Polysaccharides of baker's yeast. Part III. The presence of 1:6-linkages in yeast glucan," J. Chem. Soc. (1958) 3868-3870.

Peat, S. et al., "Polysaccharides of baker's yeast. Part IV. Mannan." J. Chem. Soc. (1961) 29-34.

Pelczar et al., Elements of Microbiology, McGraw-Hill, Inc. (1981) 35.

Phaff, H.J., "Structure and biosynthesis of the yeast cell envelope," The Yeasts, A.H. Rose et al., Eds. (1971) Chapter 5:135-210.

Sakata et al., "Stimulatory effect of short chain fatty acids on the epithelial cell proliferation in rat large intestine," Comp. Biochem. Phys. (1983) 74A(2):459-462.

Scaringi, L. et al., "Cell wall components of Candida albicans as immunomodulators: induction of natural killer and machrophage-mediated peritoneal cell cytotoxicity in mice by mannoprotein and glucan fractions," J. Gen. Microbiol. (1988) 134:1265-1274.

Schoenherr et al., "Titration of MacroGard-S on growth performance of nursery pigs," J. Animal Science (1994) 72(2):57 Abstract.

Sentandreau, R. et al., "The characterization of ligosaccharides attached to threonine and serine in a mannan glycopeptide obtained from the cell wall of yeast," Carb. Res. (1969) 10:584-585.

Sentandreau, R. et al., "The structure of a glycopeptide isolated from the yeast cell wall," Biochem. J. (1968) 109:419-432.

Shibata, N. et al., "Immunochemical properties of mannan-protein complex isolated from viable cells of Saccharomyces cerevisiae 4484-24D-1 mutant strain by the action of zymolyase," Microbiol. Immunol. (1984) 28(12):1283-1292.

Singleton, Dictionary of Microbiology & Molecular Biology, John Wiley & Sons Ltd. (1987) 389 and 391.

Valentin, E. et al., "Solubilization and analysis of mannoprotein molecules from the cell wall of Saccharomyces cerevisiae," J. Gen. Microbiol. (1984) 130:1419-1428.

Williams, D.L. et al., "A method for the solubilization of a (1→3)-β-D-glucan isolated from Saccharomyces cerevisiae," Carb. Res. (1991) 219:203-213.

Williams, D.L. et al., "Molecular weight analysis of a water-insoluble, yeast-derived (1→3)-β-D-glucan by organic-phase size-exclusion chromatography," Carb. Res. (1994) 253:293-298.

Canadian Patent Office Action for Application No. 2607004 dated Sep. 21, 2012 (2 pages).

Japanese Patent Office Action for Application No. 2008-510230 dated Oct. 30, 2012 (English Translation Only, 2 pages).

Office Action, European Patent Application No. 06759096.8, dated Mar. 18, 2014.

PRODUCTION OF BETA-GLUCANS AND MANNANS

CROSS-REFERENCE TO RELATED APPLICATIONS

This application claims priority to U.S. Provisional Application No. 60/677,973, filed May 5, 2005, the subject matter of which is hereby fully incorporated by reference.

BACKGROUND OF THE INVENTION

This invention relates to β-glucan/mannan preparations and to methods for their preparation. In particular, the invention relates to preparations, including β-(1,3/1,6) glucan and mannan, produced from microorganisms including, but not limited, to yeasts.

"Glucan" is a generic term referring to an oligo- or polysaccharide composed predominantly or wholly of the monosaccharide D-glucose. Glucans are widely distributed in nature, and are particularly important for their role in maintaining the structural integrity of bacterial, yeast, and plant cells. For example, glucan, in combination with other polysaccharides such as mannan and chitin, is responsible for the shape and mechanical strength of the cell wall. Glucans typically accounts for approximately 40% to 50% of the weight of the cell wall in these cells.

As polymers of D-glucose, the D-glucose units may be linked together in a variety of ways. For example, glucans with (1,3), (1,4), (1,6) and (1,2) linkages (glucosidic linkages) are all known. The variety of linkages possible means that glucans are normally highly branched compounds. Many forms are possible as a result of this highly variable manner in which this individual glucose units can be joined as well as the overall steric shape of the parent molecule. A common glucan is β-(1,3)-linked glucopyranose (commonly referred to as β-glucan). Cell walls of several species include β-(1,3)-linked glucopyranose coupled with β-(1,6)-linked glucopyranose. For example, the cell wall of *Saccharaomyces cerevisiae* is primarily composed of β-linked glucan, which is mainly a backbone of β-(1-3)-linked glucose units, with a minor component of inter and intra molecular branching via β-(1-6)-linkages.

Because of their chemical properties, glucans have found a wide variety of uses in the chemical, food and pharmaceutical industries. For example, they may be useful as viscosity imparting agents, emulsifiers, fibers, films, coating substances, supports for affinity chromatography and gel electrophoresis, in cell culture media, as filter pads, and in cement. They are also widely used as food thickeners and as a source of dietary fiber, and as carriers and coating agents in pharmaceutical products. Glucans have been shown to have immunopharmacological activity in humans and animals. For example, strong immunostimulation and protection against pathogenic microorganisms have been demonstrated in shrimp, fish, poultry, swine, cattle, rabbits, mice, rats and humans. Yeast β-glucans may stimulate the innate (non-specific) immune response of vertebrates and invertebrates via interaction with the Toll-like receptor Dectin-1. Such binding stimulates the production of active oxygen species in macrophages and enhances their phagocytosis and killing of microorganisms. These stimulated immune cells also produce cytokins which can circulate throughout the animal and interact with other immune cells to enhance the immune status of the animal.

The purification of β-glucans from yeast and other organisms has been extensively investigated, and a variety of methods is known. Most of these rely on the insolubility of β-(1-3)-glucan in alkali or in organic solvents. The principal known methods are: (a) high temperature extraction with concentrated sodium hydroxide, followed by high temperature extraction with acid and precipitation with ethanol (see, e.g., Manners, D. J. et al., Biochem. J. 135 19-30 (1973), Jamas, S. et al., U.S. Pat. Nos. 4,810,646, 5,028,703, and 5,250,436). Many of these protocols require preliminary homogenization of the yeast cells, and many require multiple repetition of each extraction steps; (b) extraction of yeast cell wall preparations resulting from autolysis or enzyme degradation of yeast with concentrated phenol:water (1:1) (see, e.g., U.S. Pat. No. 4,138,479 by Truscheit, E. et al.); and (c) extraction with organic solvents such as isopropanol, ethanol, acetone, or methanol either alone or in the presence of alkali (see, e.g., European Patent Application No. 515216). Acid treatment is known to reduce the number of β-(1-6)-linkages in the glucan material, which results in an increase in viscosity.

Mannan is a polymer composed of mannose units. In yeasts, mannan is associated with protein in both the external surface of the yeast cell wall, as a muscigenous polysaccharide, and in the inner cell membrane. It generally accounts for about 20-50% of the dry weight of the cell wall. Mannan is linked to a core-peptide chain as an oligomer or polymer. The complex contains about 5-50% proteins. Oligomeric mannan is bonded directly to serine and threonine, whereas polymeric mannan is bonded to aspargine via N-acetylglucosamine. In the manno-protein complex, the mannose units are linked by α-1,6, α-1,2 and α-1,3-linkages.

Mannan-oligosaccharides (MOS) can be released from yeast cell walls by proteolytic action. The released MOS can effectively bind to bacterial pathogens of the intestinal tract and block their ability to colonize the intestinal tract. For example, *E. coli*, *Salmonella* spp. and *Vibrio cholera* have proteins on their surface (lectins) which bind specifically to the mannose sugar residues of the MOS.

Considering the many uses and applications of glucans, there is a clear need in the art for a method of β-glucan/mannan extraction which avoids the use of high concentrations of alkali or acid and the use of high temperatures, which has improved recovery of glucans and mannans, and which results in a biologically useful preparation.

SUMMARY OF THE INVENTION

Figure 1:
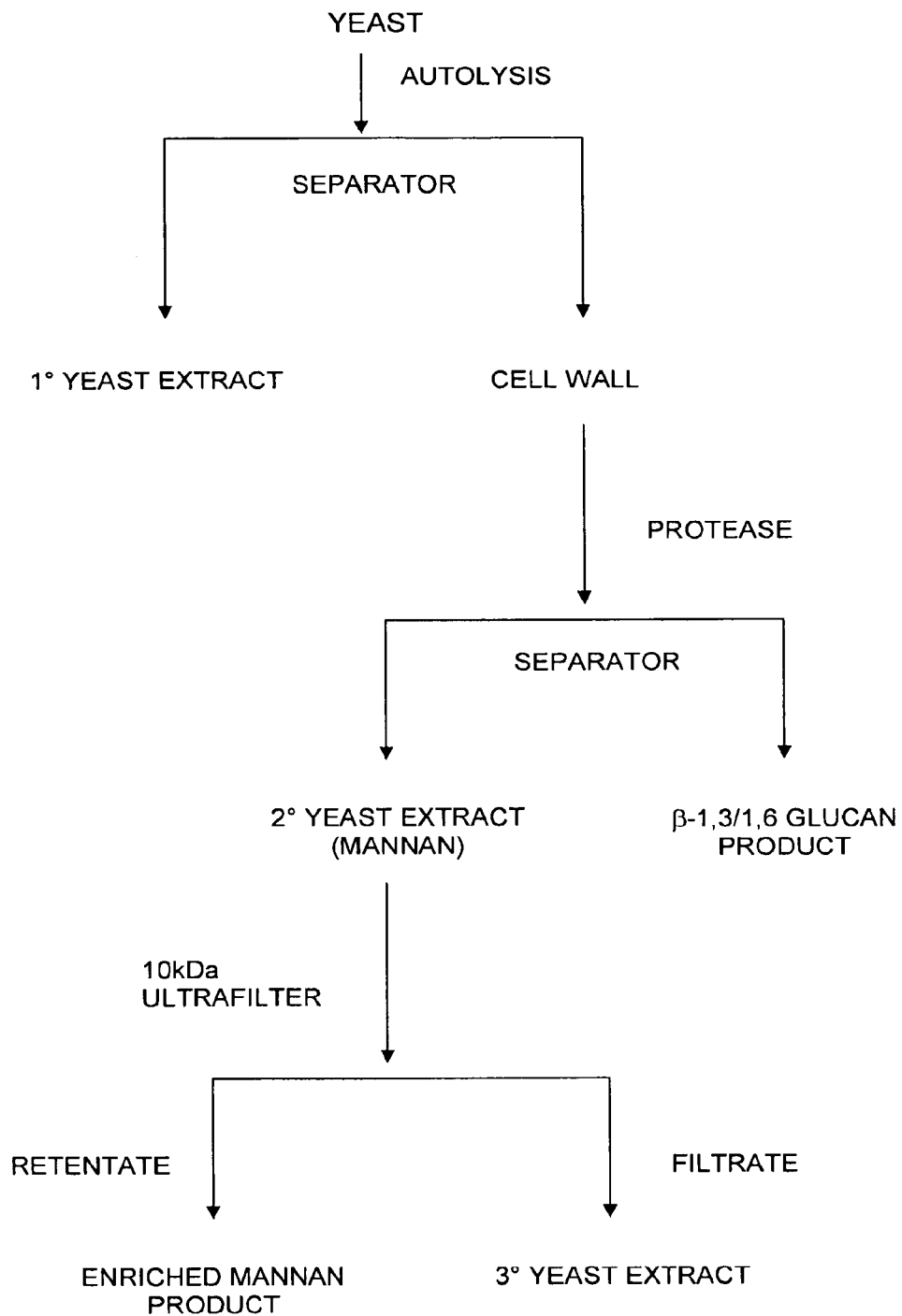
FIG. 1 is a flowchart of one embodiment of a process for production of β-glucan/mannan preparations in accordance with the present invention.

In one aspect, the present invention provides a method for processing yeast cells using the steps of autolyzing the yeast cells to release yeast cell walls, incubating the yeast cell walls with an exogenous protease, separating the yeast cell walls into a glucan-enriched component and a mannan enriched component, and ultrafiltering the mannan-enriched component to form a filtrate and a retentate.

In another aspect, the invention provides a method for processing yeast cells using the steps of autolyzing the yeast cells at a temperature of 40° C. to 65° C. to release yeast cell walls, incubating the yeast cell walls with an exogenous protease at a pH of 9 to 10, and incubating the protease-treated cell walls with an enzyme such as an amylase, lipase or a combination thereof.

In another aspect, the invention provides a composition comprising α-mannans, wherein at least 85% (w/w) of the total α-mannans have a molecular weight of 10,000 Da or more.

Other embodiments of the invention include animal feeds, food supplements, pharmaceuticals, cosmetics and neutraceuticals that comprise glucans or mannans made by methods of the invention.

BRIEF DESCRIPTION OF THE INVENTION

In one embodiment, the invention provides a process that produces insoluble cell wall preparations enriched in β (1,3) and β (1,6) glucans and a soluble fraction enriched in mannans. The process in accordance with the present invention includes an autolysis step of a source of cell walls, for example, yeast, such as brewer's yeast or baker's yeast, followed by an enzymatic digestion step. In one aspect, the enzymatic digestion is carried out using a high-pH protease. In another aspect, the enzymatic digestion is carried out using a combination of enzymes, such as a high-pH protease, an amylase, glucoamylase and/or lipase. In one embodiment, the enzymatic digestion is carried out using a high-pH protease followed by one or more other enzymes, such as amylase, glucoamylase and/or lipase.

In another embodiment the invention provides a cell wall preparation that is enriched β-(1,3) and β-(1,6) glucans, and in another embodiment, a soluble fraction enriched in mannans.

Other aspects of the invention will become apparent by consideration of the detailed description and accompanying drawings.

DETAILED DESCRIPTION OF THE INVENTION

Before any embodiments of the invention are explained in detail, it is to be understood that the invention is not limited in its application to the details of components and the arrangement of components set forth in the following description or illustrated in the drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It also is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between the lowest value and the highest value enumerated are to be considered to be expressly stated in this application.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximation, the numerical values set forth in the specific examples are reported as precisely as possible. Any numerical value, however, inherently contain certain errors necessarily resulting from the standard deviation found in their respective testing measurements.

β-glucan/mannan preparations can be prepared from microorganisms, such as yeast, using a simple autolysis process, at slightly acidic/near-neutral pH and only moderately elevated temperature. Autolysis is followed by an enzymatic digestion. In one embodiment, the enzymatic step utilizes a high pH protease (e.g., Protex 6L available from Genencore International or from fermentation of *Bacillus lichenformis*), typically about 0.05%-1% by weight, at an alkaline pH, and elevated temperature.

Suitable yeast species as a source of β-glucans/mannans include, but are not limited to, yeast strains of *Saccharomyces cerevisiae* (including baker's yeast strains and brewer's yeast strains), *Kluyveromyces fragilis*, and *Candida* strains, such as *Candida utilis*, and combinations thereof. Other strains of yeast which are suitable sources of β-glucans/mannans include, but are not limited to, *Saccharomyces delbruekii*, *Saccharomyces rosei*, *Saccharomyces microellipsodes*, *Saccharomyces carlsbergensis*, *Schizosaccharomyces pombe*, *Kluyveromyces lactis*, *Kluyveromyces polysporus*, *Candida albicans*, *Candida cloacae*, *Candida tropicalis*, *Candida guilliermondii*, *Hansenula wingei*, *Hansenula arni*, *Hansenula henricii*, *Hansenula Americana* and combinations thereof. These yeast strains can be produced using culture in food grade nutrients either by batch fermentation or continuous fermentation.

Many other species of microorganisms, including, but are not limited to, bacteria, fungi, and plants, for example, unicellular algae, have been reported in the art as a source of β-glucans/mannans. Other microorganisms which may be useful in the invention as sources of β-glucans and/or mannans include, but are not limited to, bacteria, such as *Alkaligenes*, especially *Alkaligenes faecalis* Var. mixogenes (ATCC-21680), *Agrobacterium*, *Cellulomonas*, such as ATCC 21399 and *Cellulomonas flavigena* (ATCC 53703), and *Pestalotia;* fungi, for example *Aureobasidum* such as *Aureohasidum pullulans* strain IFO446 and *Aureobasidum* species K-1 (FERM P1289), *Agaricus, Lentinus, Pleurolus ostreatus, Macrophomopsis* such as strain KOB55; *Ganoderma, Schizophylla, Fachyma hoelen, Pestalotia, Coriolus*, and combinations thereof. Non-microorganisms, such as plants, may also be useful in the invention as sources of β-glucans and/or mannans.

Specifically, the process in accordance to the present invention relates to the generation of cell wall preparations enriched in β-(1,3)-and β-(1,6)-glucan content and mannan content, produced from microorganisms including, but not limited to, yeast. In an exemplified embodiment, the process includes a first step of autolysis of yeast, e.g., brewer's yeast, (typically a 7% to 18%, particularly a 10% to 17%, and more particularly a 8% to 12% or 13% to 16% solids slurry). The autolysis may suitably be carried out at a pH of at least 4, particularly at least 4.5, and more particularly at least 5. The autolysis may suitably be carried out at a pH of less than 8, particularly less than 7, and even more particularly less than 6. The temperature for carrying out the autolysis may suitably be at least 30° C., particularly at least 35° C., more particularly at least 40° C., and even more particularly at least 45° C. The temperature for carrying out the autolysis may suitably be less than 55° C., particularly less than 52° C., and even more particularly less than 50° C. The autolysis may suitably be carried out for at least 10 hours, particularly at least 16 hours, and more particularly at least 24 hours. The autolysis may suitably be carried out for less than 100 hours, particularly less than 48 hours, and even more particularly less than 36 hours. The yeast is then separated, suitably by centrifugation, to produce an extract, and a cell wall stream of low β-glucan content. A further step treats the cell wall stream with an enzyme including, but not limited to, a protease, e.g., an alkaline protease, at a pH of at least 8.5, particularly at least 9, and more particularly at least 9.2. The pH may also suitably be less than 10.5, particularly less than 10, and even more particularly less than 9.8. The protease treatment may suitably be carried out at a temperature of at least 45° C., particularly at least 50° C., more particularly at least 53° C. The protease treatment may suitably be carried out at a temperature of less than 70° C., particularly less than 65° C., more particularly less than 60° C., and even more particularly less than 57° C. The protease treatment may be suitably carried out for at least 5 hours, particularly at least 8 hours, more particularly at least 10 hours, even more particularly at least 12 hours. The protease treatment may be suitably carried out for less than 48 hours, particularly less than 36 hours, more particularly less than 24 hours, and even more particularly less than 18 hours. The second product is then separated by centrifugation to produce an extract enriched with mannan (α-mannan), and a cell wall product enriched in β-glucan. This β-(1,3/1,6) cell wall product is then dried, e.g., spray dried, which results in aggregation of the product to particles of about 100-300 microns or larger. The mannan extract is then subjected to a 10,000 molecular weight ultrafiltration to yield a high-molecular weight retentate that is enriched in mannan.

This exemplified process described above is shown in the flowchart of FIG. 1. Live yeast are subjected to autolysis in a process in which endogenous yeast enzymes break down and solubilize some yeast macromolecules. Soluble extract is separated from insoluble yeast cell walls by centrifugation. The cell walls are then treated with a high-pH protease to further remove protein from the cell walls, and subsequently also remove the mannan which is attached to the cell wall protein. The β-glucan enriched cell walls are then separated from the secondary extract by centrifugation. Mannan, which has a high molecular weight, can be further purified and concentrated by passing the secondary extract through a 10,000 Da ultrafilter.

In another embodiment, the process includes a first step of autolysis of yeast, e.g., brewer's yeast, (typically a 8%-12% solids slurry). The autolysis is suitably carried out at a pH of at least 4, particularly at least 4.5, and more particularly at least 5. The pH may also suitably be less than 8, particularly less than 7, and even more particularly less than 6. The temperature for carrying out the autolysis may suitably be at least of at least 30° C., particularly at least 40° C., and more particularly at least 45° C. The temperature may also suitably be less than 55° C., particularly less than 53° C., and even more particularly less than 50° C. The autolysis may suitably be carried out for at least 10 hours, particularly at least 16 hours, and more particularly at least 24 hours. The autolysis may suitably be carried out for less than 100 hours, particularly less than 48 hours, and even more particularly less than 36 hours. The yeast is then separated, suitably by centrifugation, to produce an extract, and a cell wall stream of low β-glucan content. A further step treats the cell wall stream with enzymes. The enzymatic step utilizes first a high pH protease at an alkaline pH, for example, at a pH of at least 8.5, particularly at least 9, and more particularly at least 9.2. The pH may also suitably be less than 10.5, particularly less than 10, and even more particularly less than 9.8. The protease treatment may suitably be carried out at a temperature of at least 45° C., particularly at least 50° C., more particularly at least 53° C. The protease treatment may suitably be carried out at a temperature of less than 70° C., particularly less than 65° C., and more particularly less than 60° C., and even more particularly less than 57° C. The protease treatment may be suitably carried out for at least 5 hours, particularly at least 8 hours, more particularly at least 10 hours, even more particularly at least 12 hours. The protease treatment may be suitably carried out for less than 48 hours, particularly less than 36 hours, more particularly less than 24 hours, and even more particularly less than 18 hours. The protease enzymatic step is followed by incubation with glucoamylase (e.g. from *Aspergillus* species), an amylase (e.g., α-amylases from *Bacillus subtili*, *Aspergillus oryzae*; amyloglucosidases from *Aspergillus niger* or *Rhizopus* mold) and/or a lipase (e.g., lipase from *Pseudomonas cepacia*, *Candida rugosa* and *Mucor javanicus*; typically about 0.05%-1% by weight), The incubation with glucoamylase, amylase and/or lipase is suitably carried out at neutral to slightly acidic pH and elevated temperature. For example, the pH may suitably range from at least 3.5, particularly from at least 4, and even more particularly from at least 4.5. The pH may also suitably range from less than 7, particularly less than 6, and even more particularly less than 5.5. The temperature for carrying out the incubation with glucoamylase, amylase and/or lipase may suitably range from at least 40° C., particularly at least 45° C. more particularly at least 50° C. and even more particularly at least 53° C. The temperature may also suitably range from less than 70° C., particularly less than 65° C., more particularly less than 60° C., and even more particularly less than 58° C. Temperatures of at least 60° C., at least 65° C., at least 70° C., at least 75° C., at least 80° C., at least 85° C., or at least 90° C. may be suitably be used, particularly if the protease, amylase or lipase is a thermostable enzyme. The incubation with the alkaline protease can also be followed by incubation with a combination of a glucoamylase and a lipase, a combination of an amylase and a lipase or a combination of a glucoamylase, an amylase and a lipase.

The exemplified process described above is shown in the flowchart of FIG. 2. In the process depicted in FIG. 2, live yeast are subjected to autolysis in a process where endogenous yeast enzymes break down and solubilize some yeast macromolecules. The cell walls from the autolysis are first treated with the high pH-protease. The incubation with the high-pH protease is suitably carried out at a temperature of 50° to 65° C. for approximately 10 to 16 hours. The cell walls are then treated with an amylase (or other glucanase) or lipase, or a combination of amylase and lipase. The incubation with the amylase and/or a lipase is suitably carried out at a pH of 4 to 7 and a temperature of 50° to 65° C. for approximately 4 to 10 hours. The amylase may digest residual alpha-glucans such as glycogen that may still reside with the cell wall. The lipase may degrade cell wall membranes enriched with lipids and fats. The cell wall stream may then be separated by centrifugation to produce a secondary extract enriched with mannan, and a cell wall product enriched in β-glucans. The cell wall product may be dried, e.g., spray dried. The secondary mannan extract may be passed through an ultrafilter, such as a 10,000 Da ultrafilter, a 50,000 Da ultrafilter, or a 100,000 Da ultrafilter to enrich the mannan content of the retentate.

The preparations of the invention may be dried by any suitable process including, but not limited to, freeze-drying, roller drum drying, oven-drying, spray-drying, ring-drying, and combinations thereof and/or dried using film-forming equipment, and either may be used without further processing, or may be milled using any suitable technique.

Suitably, the high-pH protease may have an optimum proteolytic activity at a pH above 7. Suitable proteases include, but are not limited to, those obtained from *Actinidia chinensis, Ananas comosus, Aspergillus* spp. (e.g. *A. niger, A. niger* var. *awamori, A. oryzae, A. sojae, A. melleus*), *Bacillus* spp. (e.g. *B. subtilis, B. alcalophilus, B. amyloliquefaciens, B. halodurans, B. lentus, B. licheniformis, B. stearothermophilus, B. thermoproteolyticus), Carica papya, Cryphonectria parasitica, Endothia parasitica, Ficus glabrata, Kluyveromyces lactis, Penicillum citrinum, Rhizomucor miehei, Rhizopus niveus*, from calf, goat or ox stomachs or porcine pancreases, and combinations thereof. Suitable proteases may include, but are not limited to, commercially available enzymes such as subtilisin Carlsberg, subtilisin BPN', subtilisin Novo, subtilisin 309, subtilisin 147 and subtilisin 168, Alcalase™, Savinase™, Primase™, Duralase™, Durazym™, Esperase™, and Kannase™ (available from Novo Nordisk A/S); Maxatase™, Maxacal™, Maxapem™, Optimase™, Properase™, Purafect™, Purafect OxP™, FN2™, and FN3™ (available from Genencor International Inc.); and Validase™ AFP, Validase™ FP Concentrate, Validase™ FP 500, Validase™ FP II, Validase™ TSP Concentrate, Alkaline Protease Concentrate, Bromelain (available from Valley Research, South Bend, Ind.), and combinations thereof.

Suitable amylases include those of plant, animal, bacterial or fungal origin, and combinations thereof. Amylases include, but are not limited to, glucoamylases or α-amylases obtained from *Bacillus* spp., (e.g., *B. licheniformis, B. amyloliquefaciens, B. subtilis, B. stearothermophilus), Aspergillus oryzae, Aspergillus niger, Aspergillus niger* var. *awamori, Microbacterium imperiale, Thermomonospora viridis*, barley malt (*Hordeum* spp.), porcine pancreas (*Sus* spp.), and combinations thereof. Examples of useful amylases include, but are not limited to, commercially available amylases such as Glucoamylase Concentrate, Duramyl™, Termamyl™, Fungamyl™ and BAN™ (available from Novo Nordisk A/S); Rapidase™ and Purastar™ (available from Genencor International Inc.); and Validase™ BAA, Validase™ HT340L, Validase™ FAA, Validase™ AGS, Validase™ GA, Validase™ RGA (available from Valley Research, South Bend, Ind.), and combinations thereof. The amylase may be suitably used at a final concentration of at least 0.001%, particularly at least 0.01% and even more particularly at least 0.02%. The amylase may be suitably used at a final concentration of less than 0.1%, particularly less than 0.05%, and even more particularly less than 0.1%.

Lipases useful in the invention include, but are not limited to, lipases from *Humicola* (synonym *Thermomyces*), e.g. from *H. lanuginosa* (*T. lanuginosus*), *H. insolens*, a *Pseudomonas* lipase, e.g. from *P. alcaligenes* or *P. pseudoalcaligenes, P. cepacia, P. stutzeri, P. fluorescens, Pseudomonas* sp. strain SD 705, *P. wisconsinensis*, a *Bacillus* lipase, e.g. from *B. subtilis, B. stearothermophilus* or *B. pumilus* (WO 91/16422); *Aspergillus oryzae, Aspergillus niger, Candida lipolytica, Candida rugosa, Mucor javanicus, Penicillum roqueforti, Rhizomucor miehei, Rhizopus delemar, Rhizopus niveus, Rhizopusoryzae, Rhizopus arrhizus*, and combinations thereof. Commercially available lipase enzymes include, but are not limited to, Lipolase™ and Lipolase Ultra™ (Novo Nordisk A/S), and Fungal Lipase 8000 and Pancreatic Lipase 250 (available from Valley Research, South Bend, Ind.).

The product resulting from autolysis of the yeast cells suitably also comprises, at least 20%, particularly at least 23% and more particularly at least 25% protein of the total product on a dry solids basis. The product also suitably comprises less than 45%, particularly less than 40% and more particularly less than 35% protein of the total product on a dry solids basis. The product resulting from autolysis of the yeast cells suitably comprises at least 20%, particularly at least 23% and more particularly at least 25% total glucans of the total product on a dry solids basis. The product also suitably comprises less than 45%, particularly less than 40% and more particularly less than 35% total glucans of the total product on a dry solids basis.

The product resulting from autolysis of the yeast cells suitably comprises, at least 5%, particularly at least 7% and more particularly at least 10% alpha-glucans of the total product on a dry solids basis. The product also suitably comprises less than 20%, particularly less than 18% and more particularly less than 15% alpha-glucans of the total product on a dry solids basis. The product resulting from autolysis of the yeast cells suitably comprises, at least 7%, particularly at least 10% and more particularly at least 12% beta-glucans of the total product on a dry solids basis. The product also suitably comprises less than 22%, particularly less than 20% and more particularly less than 18% beta-glucans of the total product on a dry solids basis. The product resulting from autolysis of the yeast cells suitably comprises, at least 5%, particularly at least 7% and more particularly at least 10% mannans of the total product on a dry solids basis. The product also suitably comprises less than 20%, particularly less than 18% and more particularly less than 15% mannans of the total product on a dry solids basis.

The enriched β-(1,3/1,6) glucan product cell wall product is characterized, for example, as at least 50%, at least 55%, at least 60% or at least 65% β-(1,3/1,6) glucan with a protein content of less than 20%, less than 15%, or less than 10%. The enriched mannan product (secondary mannan extract) may be characterized as containing at least 50%, particularly at least 55% and even more particularly at least 57% mannan. The enriched mannan product may also be characterized as containing less than 70%, particularly less than 68%, and even more particularly less than 65% mannan. The enriched mannan product (secondary mannan extract) may be also characterized as containing at least 25%, particularly at least 27%, and more particularly at least 29% protein. The enriched mannan product may be also characterized as containing less than 35%, particularly less than 32%, and more particularly less than 30% protein.

The ultrafiltration step may be carried out by forcing an extract produced from the processes described herein, such as a secondary mannan extract, through an ultrafilter under pressure. Suitably, the ultrafilter comprises one or more semi-permeable membranes. The semi-permeable membrane or ultrafilter may have a molecular weight cut-off of, for example, at least 8,000 Da, particularly at least 10,000 Da, more particularly at least 25,000 Da, even more particularly at least 50,000 Da, still more particularly at least 100,000 Da, and yet still more particularly at least 150,000 Da. It is to be understood that the ultrafilter may have a molecular weight cut of any value between those recited herein including, but not limited to, a molecular weight cut off of at least 15,000 Da, 20,000 Da, 30,000 Da, 40,000 Da, 60,000 Da, 70,000 Da, 80,000 Da, 90,000 Da, 110,000 Da, 120,000 Da, 130,000 Da and 140,000 Da. Suitable ultrafilter membranes include, but are not limited to, hollow fiber membranes available from A/G Technology Corp, Needham, Mass.

At least 80% (w/w), particularly at least 85% (w/w), and more particularly at least 90% (w/w) of the total secondary mannans in the retentate following filtration of a secondary mannan extract may have a molecular weight above the molecular weight cut off of the filter used. For example, if a 10,000 Da cut off is used with a secondary mannan extract, typically at least 80% (w/w), particularly at least 85% (w/w), and more particularly at least 90% (w/w) of the total mannans in the retentate may have a molecular weight above 10,000 Da. If a 50,000 Da cut off is used with a secondary mannan extract, typically at least 80% (w/w), particularly at least 85% (w/w), and more particularly at least 90% (w/w) of the total mannans in the retentate may have a molecular weight above 50,000 Da. If a 100,000 Da cut off is used with a secondary mannan extract, typically at least 80% (w/w), particularly at least 85% (w/w), and more particularly at least 90% (w/w) of the total mannans in the retentate may have a molecular weight above 100,000 Da. If a 150,000 Da cut off is used with a secondary mannan extract, typically at least 80% (w/w), particularly at least 85% (w/w), and more particularly at least 90% (w/w) of the total mannans in the retentate may have a molecular weight above 150,000 Da.

The ultrafiltration step may optionally include passing the mannan extract through two or more ultrafilters of different molecular weight cut offs. The final retentate comprises an enriched mannan product wherein a majority of mannans have a molecular weight falling between the molecular weight cut-offs of the ultrafilters. In this embodiment, at least 80% (w/w), particularly at least 85% (w/w), and more particularly at least 90% (w/w) of the total mannans of the final retentate may suitably have a molecular weight between the molecular weight cut-offs of the ultrafilters.

The secondary mannan extract which results from separation from the glucan enriched product following enzymatic treatment of autolyzed cell walls is characterized, for example, from 15% to 50% mannan, 20% to 30% protein, and 20% to 25% other components. When the secondary mannan extract is ultrafiltered according to methods of the invention, the retentant may comprise at least 50%, particularly at least 52%, more particularly at least 55% and even more particularly at least 60% mannan. The retentate may comprise less than 70%, particularly less than 65%, and more particularly less than 62% mannan. The retentate may further comprise at least 10%, particularly at least 12%, more particularly at least 15% and even more particularly at least 17% protein. The retentate may further comprise less than 33%, particularly less than 30%, and more particularly less than 22% protein.

The preparations in accordance with the present invention are contemplated to be of value in, e.g., food supplements, pharmaceuticals (e.g., improving immune response), cosmetics, animal feeds, and neutraceuticals. For example, an animal feed may suitably contain 1 to 10g of preparation/kg feed. Suitably, the preparation may be comprise at least 0.01%, particularly at least 0.02%, more particularly at least 0.05%, and even more particularly at least 0.1% and less than 5%, particularly less than 2%, more particularly less than 0.5%, and even more particularly less than 0.3% of the total weight of the feed, on a weight/weight basis. Suitable animal feeds include, but are not limited to, cattle, horse, swine, poultry, fish (e.g., crustacean, shellfish), bird and pet (e.g., cat, dog) feeds. A liquid composition may contain 0.1%-1% by weight of the preparation in accordance with the present invention. Preparations according to the invention may also be used in a plant protection composition together with an agriculturally acceptable carrier, and optionally an agriculturally acceptable nutrient, herbicide or pesticide.

For example, the enriched beta-glucan fractions made according to the present invention may suitably be used as immune stimulators in animal and human foods, pharmaceuticals or emollients, agents to reduce cholesterol, and thickening agents in foods and beverages. If added to an emollient, lotion or cream and used to treat a condition, the beta glucan may be suitably present at a concentration (w/w) of at least 0.05%, particularly at least 0.1% and more particularly at least 0.5%, and less than 10%, particularly less than 5% and more particularly less than 2%. Suitably, the beta-glucan fractions made according to the present invention may be used to treat eczema, for example, by incorporation into a cream, lotion or emollient. Eczema encompasses various inflamed skin conditions, including atopic dermatitis ("atopic eczema"), and affects about 10% to about 20% of the world population during childhood. Eczema appears to be an abnormal response of the body's immune system.

There are also numerous uses for the mannan-enriched products made according to the present invention. For example, mannan products may be used in the animal feed industry, having advantageously the ability to bind mycotoxins and also pathogenic bacteria, preventing bacteria from colonizing the intestinal tract.

In summary, the invention provides, among other things, enriched preparations of β-glucans and mannans, utilizing processes of relatively mild process conditions.

Various features and aspects of the invention are set forth in the following examples.

EXAMPLE 1

Processing of Yeast Using a High pH Protease 31.1 kg of the cell wall fraction from a commercial autolysis of brewer's yeast (*Saccharomyces cerevisiae*) was heated to 55° C. in a jacketed stainless steel vessel. The total solids were 10.7% and the total proportion of protein in the solids was 24.5%. The pH was raised to 9.5 with sodium hydroxide and 0.1% (total weight basis) of Protex 6L (an alkaline protease, available from Genencor, Palo Alto, Calif.) was added. The cell walls were agitated at 55° C. for 16 hours. The Protex 6L was heat inactivated at 85° C. for 30 minutes and the cell walls were separated with an Alpha Laval Gyro model bowl centrifuge, using a continuously decanting process. The insoluble cell wall fraction was washed three times with a volume of water equal to the volume of extract removed. The washed cell wall fraction was condensed to 15.4% solids, the pH was adjusted to 7.0 with hydrochloric acid and the fraction was spray dried. A portion of the extract from the Protex 6L treatment (corresponding to the 2° extract shown in FIG. 1) was condensed to 28.3% solids, the pH was adjusted to 7.0 and the extract was spray dried. The remainder of the 2° extract was ultrafiltered using a UFP-10-C-6A 10,000 NMWC hollow fiber membrane (available from A/G Technology Corp, Needham, Mass.). The high molecular weight enriched mannan retentate was adjusted to pH 7.0 and spray dried. The 3° extract (filtrate) was adjusted to pH 7.0, condensed and spray dried.

The composition of the products resulting from this process were analyzed using the following techniques: protein was determined using a LECO protein determinator (LECO Corp., St. Joseph, Mich.); total glucans, alpha-glucans and beta-glucans were measured using Megazyme International Mushroom and Yeast Beta-glucan kit (available from Megazyme International, Wicklow, Ireland); mannans were determined by acid hydrolysis of carbohydrates and linked spectrophotometric assay for free mannose, using hexokinase, glucose-6-phosphate dehydrogenase, phosphoglucose isomerase and phosphomannose isomerase; fat was determined using the methanol-chloroform extraction method of Blich, E. G. and Dyer, W. J. Can. J. Biochem. Physiol. (1959) 37, 911; free glucose was measured using Yellow Springs Instruments Biochemistry Analyzer (available from YSI Incorporated, Yellow Springs, Ohio). The results of these analyses are shown in Table 1.

TABLE 1

Characterization of Products

| Product | Protein % | Ash % | Total glucans % (dry solids basis) | Alpha Glucans % (dry solids basis) | Beta-glucans % (dry solids basis) | Free Glucose % (dry solids basis) | Mannans % (dry solids basis) | Fat % (dry solids basis) |
|---|---|---|---|---|---|---|---|---|
| Starting brewer's yeast cell wall | 31.4 | 3.5 | 28.9 | 12.4 | 16.5 | 1.2 | 13.6 | ND |
| Alkaline Protease Cell Wall | 8.6 | 2.5 | 54.6 | 29.2 | 25.4 | 0.0 | 5.7 | 14.2 |
| 2° Extract | 39.9 | 10.9 | ND | ND | ND | 1.0 | 22.6 | ND |
| Ultrafilter retentate | 29.6 | 5.9 | ND | ND | ND | 0.0 | 62.7 | ND |
| 3° Extract (filtrate from ultrafiltration) | 52.3 | 13.6 | ND | ND | ND | 1.8 | 8.6 | ND |

ND means not determined.

EXAMPLE 2

Processing of Yeast using a High pH Protease and A Glucoamylase 16,000 gal of cell wall creams from a production run of brewer's yeast extract were heated to 55° C. and the pH was adjusted to 9.5 with sodium hydroxide. Protex 6L was added at 0.1% (v/v), and the mixture was held at 55° C. for 14 hours. The pH was lowered to pH 5.0 with HCl. At pH 5 the Protex 6L is inactive and will not destroy added enzymes. Glucoamylase Concentrate (available from Valley Research, South Bend, Ind.) was added at 0.0175% (weight: total weight). The temperature was held at 55° C. for 4 hours and then raised to 88° C. to inactivate the enzymes. The heated material was separated with a Westfalia bowl separator (available from Westfalia Separator, Inc., Northvale, N.J.). Most of the extract (shown as the 2° extract in FIG. 2) was condensed and spray dried. A portion of the 2° extract was ultrafiltered using a UFP-10-C-6A 10,000 NMWC hollow fiber membrane (available from A/G Technology Corp, Needham, Mass.). The retentate and the filtrate were condensed and spray dried. The spray dried products were analyzed according to the techniques described in Example 1. The results are presented in Table 2. The cell wall fraction was water washed by centrifugation, condensed and spray dried.

The effectiveness of the glucoamylase added in the process of Example 2 can be seen when comparing the data of Tables 1 and 2. In the process of Example 2, alpha-glucans were not detectable in the retentate and filtrate following ultrafiltration. Also, the 2° and 3° extracts from the process of Example 2 have a much higher level of free glucose, as shown in Table 2 than the 2° and 3° extracts from Example 1, as shown in Table 1.

EXAMPLE 3

Processing of Yeast using Glucoamylase and a High pH Protease Added to Autolyzed Yeast Cell Walls in Different Orders To each of two jacketed, stainless steel vessels was added 25 Kg of cell walls from a commercial run of a brewer's yeast extract, in which yeast cells had been subjected to autolysis. Solids were 11.8%. Both vessels were heated to 55° C. The pH of Vessel 1 was adjusted to 5.0 and Glucoamylase Concentrate (available from Valley Research, South Bend, Ind.) was added at 0.1% (weight: total weight). Incubation was continued for 14 hours before raising the pH to 9.5. 0.10% Protex 6L was then added and incubation was continued for 4 hours. Samples were taken at various time points and assayed for free glucose released by the action of the glucoamylase.

TABLE 2

Figure 2:
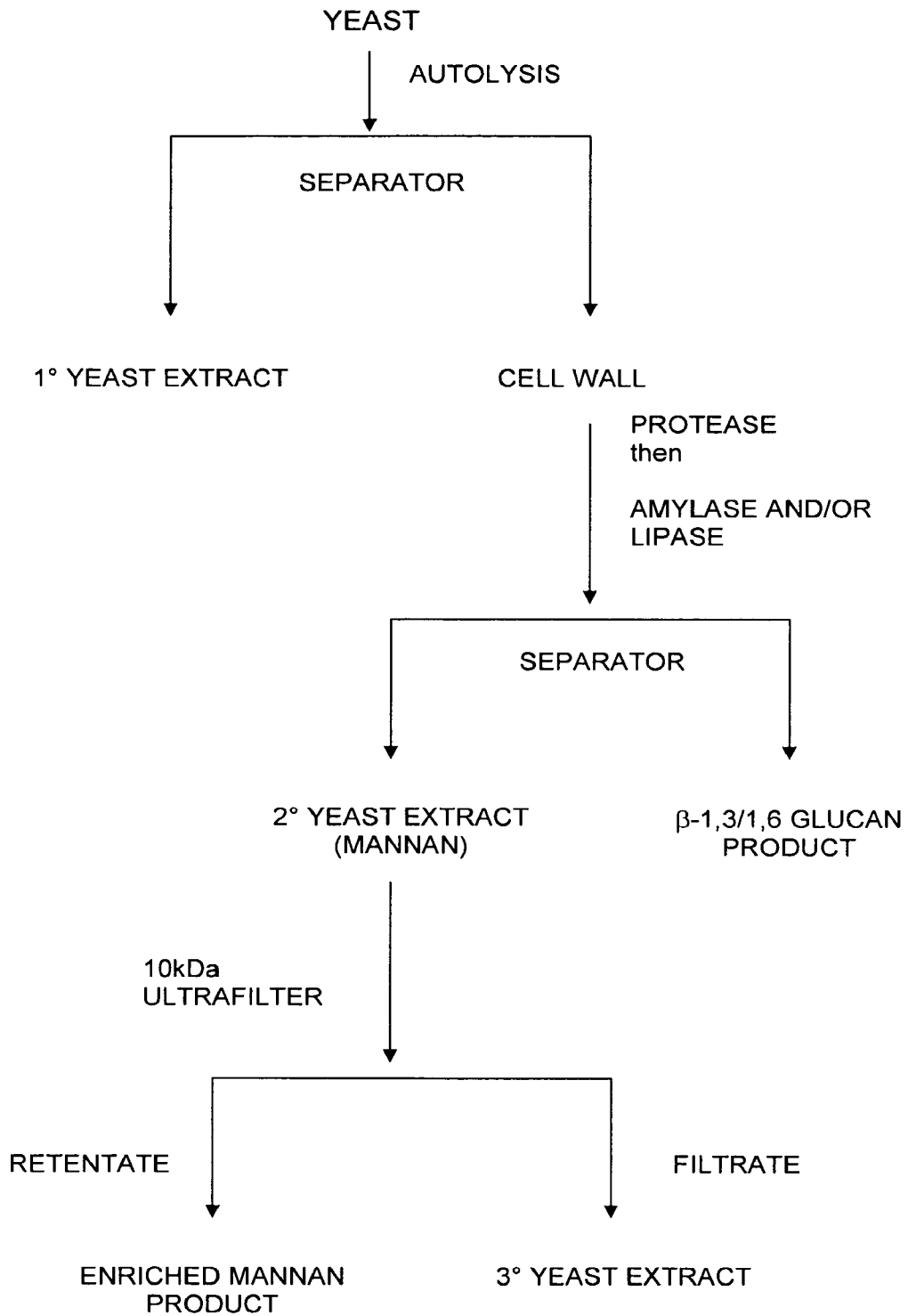
FIG. 2 is a flowchart of another embodiment for process for production of β-glucan/mannan preparations in accordance with the present invention.

Characterization of Products made according to Process Depicted in FIG. 2

| Product | Protein % | Ash % | Total Glucan % (dry solids basis) | Alpha Glucan % (dry solids basis) | Beta Glucan % (dry solids basis) | Free Glucose % (dry solids basis) | Mannan % (dry solids basis) | Fat % (dry solids basis) |
|---|---|---|---|---|---|---|---|---|
| Cell walls from enzyme treatments | 12.4 | 4.3 | 53.0 | 2.4 | 50.6 | 5.0 | 4.8 | 15.2 |
| 2° Extract | 26.4 | 11.3 | ND | ND | ND | 29.4 | 17.4 | ND |
| Ultrafilter retentate | 20.7 | 5.0 | 9.5 | 0.0 | 0.0 | 9.3 | 54.2 | ND |
| 3° extract (filtrate from ultrafiltration) | 30.1 | 12.6 | 31.6 | 0.0 | 0.0 | 33.9 | 3.5 | ND |

ND means not determined.

The pH of Vessel 2 at the start was raised to 9.5 and 0.1% Protex 6L (weight: total weight) was added. The mixture was incubated at 55° C. for 14 hours. The pH was then reduced to 5.0 and 0.1% Glucoamylase Concentrate was added at 0.1%. Incubation continued for 4 more hours. Samples were taken at various time points and assayed for free glucose released by the action of the glucoamylase. Table 3 indicates the level of free glucose in both vessels at various times.

TABLE 3

Release of glucose from α-glucans of brewer's yeast cell walls (g/L free glucose)

|  | Vessel 1 Glucoamylase then Protex 6L | Vessel 2 Protex 6L then Glucoamylase |
|---|---|---|
| Zero hours at 55° C. | 0.48 | 0.48 |
| 14 hours at 55° C. | 4.52 | 0.35 |
| 18 hours at 55° C. | 3.63 | 46.2 |

The data of table 3 indicate that when glucoamylase is added before the Protex 6L, as in Vessel 1, then the cell walls are not sufficiently altered to permit the glucoamylase to access and digest the large molecular weight α-glucan (glycogen) that is trapped inside the cell walls following the autolysis of brewer's yeast. In contrast, in Vessel 2, adding protease prior to the glucoamylase, permitted the glucoamylase to access and digest the α-glucan, and to release substantially more glucose. This is the case, even though the glucoamylase in vessel 1 had a longer time (14 hours) to work at pH 5.0 than the glucoamylase of Vessel 2 (4 hours). Therefore, for optimal removal of glycogen/α-glucan from brewer's yeast cell walls, the alkaline protease Protex 6L should be added before the glucoamylase.

EXAMPLE 4

Processing of Brewer's and Baker's Yeast According to the Process Shown in FIG. 2

220 g of the cell walls from a commercial autolysis of primary grown baker's yeast (at 15% solids) or brewer's yeast (at 11.8% solids) were heated to 55° C. and the pHs were adjusted to 9.5. The cell walls were then treated for 14 hours with 0.1% (weight: total weight) Protex 6L. After 14 hours the pHs were lowered to 5.0 and 0.0175% Glucoamylase Concentrate was added to each of the vessels. The flasks were incubated at 55° C. for an additional 4 hours. Free glucose was monitored with a YSI Biochemistry Analyzer. The results are shown in Table 4.

TABLE 4

Comparison of Glucose Released From Baker's and Brewer's Yeast Cell Walls Using the Process Shown in FIG. 2.

| % Free Glucose (dry solids basis) | Baker's Yeast Cell Walls | Brewer's Yeast Cell Walls |
|---|---|---|
| At Start | 0.0 | 0.41 |
| After Protex 6L | 0.0 | 0.30 |
| After Glucoamylase | 1.2 | 39.2 |

The cell walls resulting from the autolysis of baker's yeast contain lower levels of glycogen than do the cell walls from brewer's yeast, because primarily, aerobic grown baker's yeast tend to accumulate less beta-glucan than anaerobically grown brewer's yeast. More glucose was released from brewer's yeast cell walls following incubation with glucoamylase that from baker's yeast cell walls. The process of FIG. 2 is therefore extremely effective for processing beta-glucan from brewer's yeast cell walls.

EXAMPLE 5

Use of Extracts in Animal Feed

A 50:50 (dry solids basis) blend of autolyzed brewer's yeast cells: 2° extract from the process of FIG. 2, made according to Example 2 (i.e. mannans obtained prior following protease and amylase treatment), was formulated by dry blending the two components together. This blend was used to supplement the diets of nursery pigs for 28 days post weaning. The blend was added at 3 lbs/ton of diet during Phase 1 (0-7 days), 2 lbs/ton of diet during Phase 2 (7-14 days) and 2 lbs/ton of diet during Phase 3 (14-28 days). Both control and treatment diets contained antibiotics. Post-weaned pigs (17-22 days old) were randomly allotted to the control diet or treatment diet based on body weight. There were 6 pens with 13 pigs for each diet. The results are shown in Table 5.

TABLE 5

Body Weight, lb. (mean)

| | Days | | | |
|---|---|---|---|---|
| Treatment | 0 | 7 (end of Phase 1) | 14 (end of Phase 2) | 28 (end of Phase 3) |
| Control | 12.22 | 14.02 | 18.35[a] | 32.63 |
| 50:50 Crude cell wall:extract | 12.22 | 14.03 | 19.69[b] | 33.88 |

[a,b]Means significantly differ, P < 0.10.

Pigs fed the treatment diet were significantly heavier on day 14 and there was a tendency for the pigs to show increased in weight for the 28 days.

EXAMPLE 6

Use of Yeast Extracts as a Palatability Enhancer in Animal Feeds

Kibbles for canines were coated with oil and then either 1.0% of dry 3° extract from the process shown in FIG. 2, made according to Example 2 (i.e. the filtrate following ultrafiltration), or 1.0% of an accepted canine palatability enhancer was applied by spraying onto the surface of oil coated kibbles. 1000 g of each ration was offered to a panel of 20 dogs for two days. Bowl positions were reversed daily to prevent "left-right" bias.

The amount of food taken by each dog over the two-day period is shown in Table 6. Table 6 indicates that the 3° extract of the process of FIG. 2, made according to Example 2, enhanced the palatability of a dry dog food at least as much as, if not more than, the standard palatant.

TABLE 6

| | | 1.0% 3° Extract | | 1.0% Standard Palatant | |
|---|---|---|---|---|---|
| DOG # | WT. Kg. | DAY 1 | DAY 2 | DAY 1 | DAY 2 |
| 1 | 22.7 | 366 | 178 | 125 | 325 |
| 2 | 32.0 | 385 | 591 | 180 | 40 |
| 3 | 27.2 | 879 | 1000 | 65 | 119 |
| 4 | 22.4 | 2 | 670 | 571 | 0 |

TABLE 6-continued

| DOG # | WT. Kg. | 1.0% 3° Extract | | 1.0% Standard Palatant | |
|---|---|---|---|---|---|
| | | DAY 1 | DAY 2 | DAY 1 | DAY 2 |
| 5 | 23.3 | 34 | 274 | 656 | 438 |
| 6 | 21.9 | 412 | 576 | 4 | 0 |
| 7 | 29.1 | 456 | 219 | 111 | 374 |
| 8 | 25.3 | 561 | 455 | 68 | 148 |
| 9 | 24.6 | 83 | 400 | 622 | 431 |
| 10 | 25.4 | 382 | 507 | 126 | 191 |
| 11 | 22.9 | 683 | 696 | 187 | 288 |
| 12 | 28.1 | 278 | 2 | 221 | 583 |
| 13 | 25.0 | 0 | 672 | 300 | 0 |
| 14 | 26.6 | 53 | 0 | 341 | 425 |
| 15 | 36.8 | 89 | 444 | 642 | 406 |
| 16 | 22.5 | 560 | 536 | 149 | 69 |
| 17 | 28.9 | 286 | 394 | 98 | 0 |
| 18 | 22.0 | 220 | 494 | 309 | 184 |
| 19 | 24.8 | 320 | 4 | 1 | 391 |
| 20 | 16.8 | 220 | 470 | 265 | 50 |
| TOTAL | 508.3 | | | | |
| TOTAL per day | | 6269 | 8582 | 5041 | 4462 |
| GRAND TOTAL | | 14851 = 14.6 g/Kg/day | | 9503 = 9.3 g/Kg/day | |

EXAMPLE 7

(Prophetic) Characteristics of Yeast Cell Wall—Spray Dried Powder

A highly purified yeast cell wall product of *Saccharomyces cerevisiae* is produced according to the process described in Example 2. It has a high concentration of ($\beta$-1,3/1,6) glucan. The product is G.R.A.S. (Generally Recognized as Safe) by the FDA. The product can be used to supplement in a wide variety of foods with a high quality natural source of ($\beta$-1,3/1,6) glucan. This biologically active material has been shown to stimulate the immune system of a wide range of animals. The composition and characteristics of the product are shown in Table 7.

TABLE 7

| Characteristics | Value/Average | Method |
|---|---|---|
| Chemical | | |
| $\beta$-1,3/1,6 glucan | 50.0% Minimum | Megazyme Method |
| Protein (N × 6.25) | 15.0% Maximum | Perkin Elmer |
| Moisture | 6.0% Maximum | Standard method |
| pH (10% Solution) | 5 ± 0.3 | pH Meter |
| Microbiological | | |
| Total Bacterial Count | 15,000/g Max. | BAM |
| Yeast and Mold | 100/g Max. | BAM |
| Coliform Organisms | 10/g Max. | BAM |
| *E. Coli* | Negative | BAM |
| *Salmonella* | Negative | BAM |

EXAMPLE 8

Prophetic

Brewer's yeast cell wall cream is heated to 131° F. (55° C.). The pH is raised to 9.5 with 50% sodium hydroxide (about 5 ml per Kg of cell wall cream). Protex 6L (Genencore) is added to 0.1% (vol: total weight of cell wall cream). The mixture is held at 131° F. for 14 hours. The pH is lowered to 5.0 with 28% HCl (muriatic acid) and 0.0175% (weight: total weight) Glucoamylase Concentrate (Valley Research) is added. The mixture is held at 55° C. for 4 hours, before heat inactivating the enzymes by heating to 185-195° F. The fractions are separated. Prior to spray drying the beta-glucan enriched insoluble fraction, the pH is adjusted to 6.5. The beta-glucan enriched insoluble fraction is spray dried.

A highly purified yeast cell wall product of *Saccharomyces Cerevisiae* is produced. It has a high concentration of ($\beta$-1,3/1,6) glucan. The product is a G.R.A.S. by the FDA. The product can be used to supplement in a wide variety of foods with a high quality natural source of ($\beta$-1,3/1,6) glucan. This biologically active material has been shown to stimulate the immune system of a wide range of animals. The composition and characteristics of the product are shown in Table 7.

EXAMPLE 9

Processing of Yeast using a High pH Protease and a Lipase 220 g of cell walls (at 15% solids) from a commercial baker's yeast autolysis were placed in a glass flask and stirred. The temperature was raised to 55° C. and the pH raised to 9.5 with HCl. 0.1% Protex 6L was added and the sample was incubated for 14 hours. At this time, 30 g aliquots were dispensed into 50 ml centrifuge tubes (available from Nalgene) suitable for use in a Sorvall SS34 centrifuge rotor. A magnetic stirring bar was added to each tube. The following additions, A, B or C, were made to the centrifuge tubes:

A. 0.0175% Glucoamylase Concentrate (available from Valley Research)

B. 0.1% Lipase CR (a triacylglycerol lipase available from Valley Research)

C. 0.0175% Glucoamylase Concentrate+0.1% Lipase CR.

Each tube was incubated at 55° C. for four hours with stirring. The enzymes were heat killed at 85° C. for 15 minutes, and the cell walls were pelleted using a Sorvall™ centrifuge with a SS34 rotor (at 12,000 r.p.m. for 10 min). The pellets were then washed three times with a volume of water equal to the volume of soluble extract removed. The cell walls were resuspended to about 15% solids and spray dried with a Buchi Mini Spray Dryer B-191. The dried cell walls were analyzed for protein (nitrogen X 6.25; LECO protein determinator, available from LECO Corp., St. Joseph, Mich.) and beta-glucan was measured using Megazyme International Mushroom and Yeast Beta-glucan kit (available from Megazyme International, Wicklow, Ireland). The results are shown in Table 8.

TABLE 8

| Enzyme treatment for 4 hours after Protex 6L | Protein % | Beta-glucan % (dry solids basis) |
|---|---|---|
| A: Glucoamylase Concentrate | 34.2 | 27.3 |
| B: Lipase CR | 34.3 | 27.1 |
| C: Glucoamylase Concentrate plus Lipase CR | 30.5 | 30.8 |

EXAMPLE 10

(Prophetic) Use of the Beta-Glucan Enriched Product of Example 2 in Broiler Chicken Feed Standard chicken feed (without antibiotics) either containing 1 g/Kg of beta-glucan enriched product of Example 2, or containing no beta-glucan (control), is fed daily to broiler chickens from age day 1. After 7 days both the control and the beta-glucan fed chicks are given a respiratory challenge with a strain of *E. coli* pathogenic for chickens. The chicks are continued on their respective diets, and mortality is recorded for one month.

The mortality of the beta-glucan fed chickens is expected to be significantly lower than that for those on the standard feed. The beta-glucan stimulation of the immune system of the chickens is valuable for decreasing production losses due to respiratory infection.

EXAMPLE 11

(Prophetic) Use of the Mannan Enriched Ultrafiltrate Retentate of Example 1 in Broiler Chicken Feed Standard chicken feed (without antibiotics) either containing 1 g/Kg of the enriched mannan ultrafiltration retentate of Example 1, or containing no enriched mannan (control), is fed daily to broiler chickens for two weeks. The broiler chickens (both the control and the mannan fed groups) are then given an oral inoculation of a strain of *Salmonella* pathogenic for the chickens. The chickens are continued on their respective diets, and mortality and morbidity are monitored for one month.

The mannan binds to the *Salmonella* and prevents it from binding to the intestinal tract of the chickens on the mannan feed. This is expected to result in a significant reduction in morbidity and mortality for the mannan fed chickens.

EXAMPLE 12

(Prophetic) Use of the Beta-Glucan Enriched Product of Examples 1 or 2 in Tiger Shrimp Cultivation One group of tiger shrimp (*Penaeus monodon*) are immersed in a solution that does not contain enriched beta-glucan (control group). This group is fed a commercial pellet not containing enriched beta-glucan during the course of the study. A second group of tiger shrimp are immersed in a solution containing 0.1% of the enriched beta-glucan from Example 1, and then fed a commercial pellet containing 0.1% of the enriched beta-glucan from Example 1. A third group of tiger shrimp are immersed in a solution containing 0.1% of the enriched beta-glucan from Example 2, and then fed a commercial pellet containing 0.1% of the enriched beta-glucan from Example 2. The mortality of each group is monitored over several months.

There is historically a high rate of mortality in shrimp rearing. The yeast beta-1,3-1,6-glucans from Examples 1 and 2 are each expected to stimulate the immune response of shrimp when the shrimp are immersed in solutions containing beta-glucan, and when the shrimp are subsequently fed a feed containing beta-glucan, compared with the control group. The groups of tiger shrimp immersed in and fed the yeast beta-glucan diets are expected to grow faster and are expected to have reduced mortality compared with the control group, due to the stimulation of their innate immune systems.

EXAMPLE 13

(Prophetic) Use of the Beta-Glucan Enriched Product of Example 2 in Treatment of Eczema A select group of children suffering from eczema that is not responsive to current accepted skin lotion treatments is treated with a lotion containing a 1% suspension of the enriched β-glucan product of Example 2. The lotion is applied twice daily. The skin is evaluated weekly by a dermatologist for improvement of lesions and pain. The β-glucan lotion is expected to decrease the lesions associated pain and quickens the healing of the lesions.

EXAMPLE 14

(Prophetic) Use of the Beta-Glucan Enriched Product of Example 2 in the Production of Healthy Snack Foods Yeast beta-glucan extract from Example 2 is added to ice-cream at 1% (w/w) as a partial replacement for fat. The beta-glucan adds a firmness and body to the ice-cream without affecting the texture. The beta-glucan supplemented ice-cream contains fewer calories than ice-cream not containing beta-glucan. Upon ingestion of the supplemented ice-cream, the beta glucans are expected to stimulate the innate immune system of the intestinal tract and benefit the immune status of the consumer.

The yeast beta-glucan extract from Example 2 is added at 0.5% (w/w) and 1% (w/w) to cookies, snack bars and bakery items. The beta-glucan supplemented cookies, snack bars and bakery items contain fewer calories than cookies, snack bars and bakery items not containing beta-glucan. Upon ingestion of the supplemented cookies, snack bars and bakery items, the beta glucans are expected to stimulate the innate immune system of the intestinal tract and benefit the immune status of the consumer.

While the present invention has now been described and exemplified with some specificity, those skilled in the art will appreciate the various modifications, including variations, additions, and omissions that may be made in what has been described. Accordingly, it is intended that these modifications also be encompassed by the present invention and that the scope of the present invention be limited solely by the broadest interpretation that lawfully can be accorded the appended claims.

All patents, publications and references cited herein are hereby fully incorporated by reference. In case of conflict between the present disclosure and incorporated patents, publications and references, the present disclosure should control.

What is claimed is:

1. A method for processing yeast cells comprising:
   (a) autolyzing the yeast cells at a temperature of 50° C. to 65° C. to release yeast cell walls;
   (b) incubating the cell walls with an exogenous protease at a pH of 9 to 10;
   (c) incubating the protease-treated cell walls of step (b) with an enzyme comprising at least one of an amylase, lipase and a combination thereof;
   (d) separating the enzyme-treated cell walls of step (c) into a glucan-enriched component and a mannan-enriched component; and (e) separately retaining said glucan-enriched component and said mannan-enriched component;

wherein said glucan-enriched component of step (e) can be added to an animal feed or to a product selected from a food supplement, pharmaceutical, cosmetic and neutraceutical.

2. The method of claim 1, wherein the yeast cells comprise brewer's yeast cells.

3. The method of claim 1, wherein step (c) is carried out at a pH of 4 to 6.

4. The method of claim 1, further comprising adding the glucan-enriched component of step (e) to a product selected from a food supplement, pharmaceutical, cosmetic and neutraceutical.

5. The method of claim 1, further comprising
(f) ultrafiltering the mannan-enriched component of step (e) to form a filtrate and a retentate.

6. The method of claim 1, wherein the retentate comprises mannans, and wherein at least 85% (w/w) of the mannans have a molecular weight of at least 10,000 Da.

7. The method of claim 5, further comprising adding the filtrate of step (f) to a product selected from a food supplement, pharmaceutical, cosmetic and neutraceutical.

\* \* \* \* \*